United States Patent
Juergens et al.

(10) Patent No.: US 11,445,899 B2
(45) Date of Patent: Sep. 20, 2022

(54) USER ASSISTANCE SYSTEM FOR REUSABLE MEDICAL DEVICES

(71) Applicant: OLYMPUS WINTER & IBE GMBH, Hamburg (DE)

(72) Inventors: Thorsten Juergens, Hamburg (DE); Kristin Rosenkranz, Seevetal (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 326 days.

(21) Appl. No.: 16/881,093

(22) Filed: May 22, 2020

(65) Prior Publication Data

US 2020/0281453 A1  Sep. 10, 2020

Related U.S. Application Data

(63) Continuation of application No. PCT/EP2018/080757, filed on Nov. 9, 2018.

(30) Foreign Application Priority Data

Nov. 23, 2017 (DE) .......................... 102017127718.8

(51) Int. Cl.
*A61B 90/96* (2016.01)
*A61B 1/12* (2006.01)
(Continued)

(52) U.S. Cl.
CPC .......... *A61B 1/121* (2013.01); *A61B 1/00045* (2013.01); *A61B 1/00057* (2013.01);
(Continued)

(58) Field of Classification Search
None
See application file for complete search history.

(56) References Cited

U.S. PATENT DOCUMENTS

2006/0070934 A1* 4/2006 Bennett .................. A61L 2/087
  209/942
2011/0117025 A1 5/2011 Dacosta et al.
(Continued)

FOREIGN PATENT DOCUMENTS

| DE | 102014217559 A1 | 3/2016 |
|---|---|---|
| JP | 2009-291308 A | 12/2009 |
| WO | 2015/175681 A1 | 11/2015 |

OTHER PUBLICATIONS

International Search Report dated Jan. 24, 2019 issued in PCT/EP2018/080757.

*Primary Examiner* — Eileen M Adams
(74) *Attorney, Agent, or Firm* — Scully, Scott, Murphy & Presser, P.C.

(57) ABSTRACT

A user assistance system for reusable medical devices and a method for monitoring processing. The user assistance system includes data glasses and a data memory in which a plurality of type datasets are saved that each include information relating to an identifying feature of a specific medical device type, and information relating to instructions for reprocessing these medical device types. The user assistance system records a user identifying feature and activates an associated user profile, to record a location identifying feature and to activate an associated location profile, and to display, as visual information, instructions assigned to the active user profile and the active location profile for reprocessing the medical device.

20 Claims, 4 Drawing Sheets

(51) Int. Cl.
*A61B 90/98* (2016.01)
*A61B 1/00* (2006.01)
*A61B 1/04* (2006.01)
*G02B 27/01* (2006.01)

(52) U.S. Cl.
CPC .......... *A61B 1/00059* (2013.01); *A61B 1/043* (2013.01); *A61B 90/96* (2016.02); *A61B 90/98* (2016.02); *G02B 27/017* (2013.01); *G02B 2027/0138* (2013.01); *G02B 2027/0141* (2013.01); *G02B 2027/0178* (2013.01)

(56) References Cited

U.S. PATENT DOCUMENTS

| | | | |
|---|---|---|---|
| 2014/0145915 A1 | 5/2014 | Ribble | |
| 2017/0039423 A1* | 2/2017 | Cork | G06F 3/167 |
| 2017/0172398 A1 | 6/2017 | Carlson | |
| 2018/0286511 A1* | 10/2018 | Sukigara | G16H 20/10 |

\* cited by examiner

USER ASSISTANCE SYSTEM FOR REUSABLE MEDICAL DEVICES

CROSS-REFERENCE TO RELATED APPLICATION

The present application is a continuation of PCT/EP2018/080757 filed on Nov. 9, 2018, which is based upon and claims the benefit to DE 10 2017 127 718.8 filed on Nov. 23, 2017, the entire contents of each of which are incorporated herein by reference.

BACKGROUND

Field

The present disclosure relates to a user assistance system for reusable medical devices, a method for monitoring the processing of reusable medical devices, and a computer program.

Prior Art

Reusable medical devices such as for example endoscopes must be processed after their use for hygienic reasons. To this end, the manufacturer of the reusable medical devices provides the users with processing information which contains the necessary instructions and information for successfully processing the medical devices.

Frequently, this processing information exists as printed material, for example as printed instructions for use or as a processing card. Sometimes the processing information is also provided online.

For each type of reusable medical device, specific processing information must be provided which results in a large number of instructions for use that are always being used.

If the instructions for use exist for example as printed material, the user needs at least one free hand for handling. Even if the instructions for use are for example saved on a tablet, this does not markedly simplify handling since the user must operate the tablet in this case. In both cases, it is difficult for the user to simultaneously read the instructions and perform them. This renders processing more complex, and the instructions may not be correctly implemented.

User assistance systems are known in which the personnel are helped with processing by means of data glasses. Such a user assistance system is for example disclosed in DE 10 2014 217 559 A1. With this system, a camera installed in data glasses record an identifying feature of a specific type of surgical instrument. The generated image data are compared with identifying features saved on a data memory and, given correspondence, visual information relating to instructions for cleaning this special type of surgical instrument is displayed on a projection surface of the data glasses. When using the system, the user has both hands free in order to directly implement the instructions. Moreover, it is unnecessary to search out specific instructions for use.

SUMMARY

An object is to present a user assistance system for reusable medical devices and a method for monitoring the processing of reusable medical devices by which fast and safe processing of reusable medical devices can be achieved.

Such object can be achieved with a user assistance system for reusable medico devices comprising data glasses with a camera, an imaging optical module with a projection surface, wherein the user assistance system furthermore comprises a data memory in which a plurality of type datasets are saved that each comprise information relating to an identifying feature of a specific medical device type, and information relating to instructions for reprocessing these medical device types, wherein:

the imaging optical module is configured to project visual information onto the projection surface arranged within the field of vision of a user of the data glasses, the user assistance system is configured to record an image of a reusable medical device with the camera, to compare the image data of the image with the information relating to the identifying features in the type datasets, to identify a type of the reusable medical device using an identifying feature available within the image, and to activate a type profile assigned to an associated type dataset, wherein the user assistance system is furthermore configured to:

record a user identifying feature and compare it with user datasets saved on the data memory which each comprise information relating to at least one user identifying feature and, in the event of correspondence, to activate a user profile assigned to the user dataset, record a location identifying feature and compare it with location datasets saved on the data memory which each comprise information relating to at least one location identifying feature and, in the event of correspondence, to activate a location profile assigned to the location dataset, wherein the data memory comprises information relating to instructions for reprocessing medical devices that are assigned to at least one type profile, at least one user profile and at least one location profile, and wherein the instructions for reprocessing the medical device assigned to the active type profile, the active user profile and the active location profile are displayed as visual information on the projection surface.

In the context of the present description, the term "instructions" is understood to include handling instructions that help the user to process the medical device by means of text, images, videos or the like appearing on the projection surface. The instructions can for example be information or warnings.

A "type profile" is understood to include information on configuring the user assistance system. When the type profile is activated, the user assistance system can be configured according to this information. The terms user profile and location profile are to be understood in an analogous manner.

Advantageously, the user assistance system can offer improved handling in comparison to instructions for use. Also, only such visual information relating to instructions on processing a reusable medical device can be displayed on the projection surface of the s data glasses by the user system which are contextually related with the medical device type, the user of the data glasses, and the location at which the user is present. Accordingly, the displayed information can initially depend on which type of reusable medical device is to be processed. In addition, the displayed information can also depend on which user is wearing the data glasses. An employee who for example is responsible for sterilizing a medical device can only be shown information that is relevant for sterilizing the medical device. Information that, in contrast, is only relevant for an employee who prepares the medical devices for use in the operating room in contrast does not appear. In this way, no superfluous information appears within the field of vision of the user so that he does not first have to search for the information that is relevant to him.

In order to more strongly restrict the displayed information to the actually relevant information, the recognition of the current location can be additionally carried out using the location identifying features. The information displayed on the projection surface of the data glasses can therefore be dependent on the context of the current location. Accordingly, for example, different information appears at a sink than at a processing machine.

No information can appear if a type profile or user profile is not activated. This prevents unauthorized use of the system. However, it can also be provided that certain information such as warning instructions always appears independent of the active type profile, user profile or location profile.

In one embodiment, the data memory can be arranged within the housing of the data glasses. In another embodiment, the data memory can be arranged in a separate server that is connected to the data glasses by a wireless data connection. Such a separate server is for example described in DE 10 2014 217 559 A1.

The location identifying feature can be saved in an RFID or NFC transponder, encoded in a barcode or a data matrix code, and/or can have an external appearance of at least one stationary object.

In the event that at least one location identifying feature is saved in an RFID or NFC transponder, the data glasses can have a receiver for receiving RFID or NFC signals. The location identifying feature can be a machine-readable code, for example a linear code (such as a GS1-128 barcode), a two-dimensional code (such as a data matrix code) or a three-dimensional code as well. Likewise, symbols and/or characters can be used. If at least one location identifying code feature is encoded for example in a barcode or a data matrix code (QR code), the camera can be configured to record, and the user assistance system can be configured to evaluate, this code. If at least one location identifying feature is an external appearance of at least one stationary object, the camera can be configured to record an image of this at least one stationary object, and the user assistance system can be configured to analyze the image data of this image. Known techniques of image analysis can be used for the analysis.

The user identifying feature can be a password and/or biometric feature of the user. The password can for example be manually entered using a user interface on the data glasses, and/or it can be a spoken word. In the latter case, the data glasses can be equipped with a microphone for recording the acoustic signals, and the user assistance system can be configured for speech recognition by analyzing the recorded acoustic signals. The biometric feature can for example be a fingerprint, an iris pattern, a retina pattern, or the voice of a user. To record the fingerprint, the user assistance system can be configured with a device for recording a fingerprint and therefore comprises a fingerprint scanner, for example. To record a biometric feature in the eye region of the user, the data glasses can be for example equipped with at least one additional camera that is configured to record an image of the eye region of the user while the user is using the data glasses. Alternatively, only one camera can also be provided that can record both the eye region of the user as well as the region of the user's field of vision. A microphone can be provided on the housing of the data glasses for recognizing voice. Different than with the spoken password, the user assistance system may not be configured to perform speech recognition in this case but rather to perform voice recognition. The user assistance system can be configured both for performing speech recognition as well as voice recognition.

According to another embodiment, the user assistance system can be configured to output instructions relating to the reprocessing of the medical device as visual information and to monitor execution of these instructions by evaluating the image data recorded by the camera, wherein the user assistance system can be configured to output an error message in the event that the instruction is incorrectly executed.

Such instructions can for example relate to the cleaning of the medical device with a brush. For example, a certain channel of an endoscope must be brushed 10 times. By recording the image data with the camera and evaluating this image data, the user assistance system can recognize if this instruction has been correctly executed. If for example brushing only occurs 9 times, the user assistance system can output an error message on the projection surface of the glasses.

The instructions can however also be information relating to the correct assignment of the corresponding connections to an endoscope in an endoscope processing device. The user assistance system can check in this case if all the connections have been correctly connected.

The user assistance system can comprise a light source that emits within a wavelength range in which medical contaminants, such as bodily fluids that contain proteins such as for example blood or mucus, are excited to fluoresce, wherein the camera can be configured to record images within a wavelength range in which the fluorescence of the medical contaminants occurs, wherein the user assistance system can be further configured to generate fluorescent images, such as to amplify fluorescent images, and to show them on the projection surface.

This can allow the monitoring of the success of processing to be improved because bodily fluids that contain proteins (such as for example blood or mucus) are rendered visible which otherwise may not have been discernible. In this way, it can be checked if the processing of a reusable medical device was performed successfully.

Navigation within the visual information that appears on the projection surface can be controlled by recognizing eye movements, gesture recognition, speech recognition and/or by mechanically actuating an input element on the housing of the data glasses.

Navigation within the visual information can comprise changing pages, selecting information elements or confirming inputs. To recognize eye movements, the user assistance system can comprise for example one of the above-described cameras for recording the eye region of the user. Moreover, it can be configured to analyze the recorded image data and for example to determine where the user is looking. For gesture recognition, the user assistance system can be configured to analyze the image data recorded by the camera, wherein the image data are for example compared with gesture movements previously saved on the data memory. This for example makes it possible to change the information appearing on the projection surface by means of a signaling movement, for example to change from one page to the next.

According to another embodiment, the user assistance system can be configured to record and document the ongoing and completed reprocessing procedures, wherein the user assistance system can further comprise an external data memory that is configured to save the information relating to the ongoing and completed reprocessing procedures.

The information relating to the ongoing and completed reprocessing procedures can comprise information on the status of the reprocessing procedure, i.e., if it is completed, is being performed, or has not yet started. Moreover, the information also can comprise the time of the beginning and the end of the reprocessing procedure, the type of the medical device, the user who is performing the reprocessing procedure, the location and/or information about which reprocessing step it is.

The external data memory can be the same data memory on which the instructions for processing medical devices are also saved, provided that the latter is also an external data memory. They can, however, also be two separate data memories. The safety of processing may be increased by saving the documentation on an external data memory since the information is saved beyond the direct access of the user. The information saved on the external data memory can always be retrievable by at least one workplace configured for this. Consequently, the processing of a reusable medical device can be traced at any time from this workplace.

According to another embodiment, the user assistance system can be configured to assign a designated processing time to at least one reprocessing procedure and to display a remaining duration of the designated processing time on the projection surface, wherein the user assistance system can be configured to display information relating to a position of a medical device whose designated processing time has expired upon the expiration of the designated processing time.

Such a display may be for example useful in the processing of endoscopes. For example, several endoscopes can be processed in different racks of a processing device, or possibly several processing devices as well. Each endoscope can be assigned a designated processing time. The remaining duration of this designated processing time can then be displayed on the projection surface. After the designated processing time has expired, the data glasses show for example the rack in which the associated endoscope is located, or the position of the rack can be displayed on the projection surface of the data glasses directly in the user's field of vision.

Such object can also be achieved by a method for monitoring the processing of reusable medical devices, wherein a plurality of type datasets for different types of reusable medical devices and information relating to instructions on the reprocessing of these medical device types can be saved in a data memory, and information can be present in each type dataset relating to an identifying feature of a specific medical device type, wherein visual information is projected onto a projection surface arranged in the field of vision of a user of data glasses, wherein at least one image of the reusable medical device is recorded with a camera, the image data of the image are compared with the information relating to the identifying features in the type datasets, a type of the reusable medical device is identified using an identifying feature available within the image, and a type profile assigned to an associated type dataset is activated, wherein the method comprises:

a user identifying feature is furthermore recorded and compared with user datasets saved on the data memory which each comprise information relating to at least one user identifying feature and, in the event of correspondence, a user profile assigned to the user dataset is activated, wherein furthermore a location identifying feature is recorded and compared with location datasets saved on the data memory which each comprise information relating to at least one location identifying feature and, in the event of correspondence, a location profile assigned to the location dataset is activated, wherein the data memory comprises information relating to instructions for reprocessing the medical device that are assigned to at least one type profile, at least one user profile and at least one location profile, and wherein the instructions for reprocessing the medical device assigned to the active type profile, the active user profile and the active location profile are displayed as visual information on the projection surface.

The same or similar advantages apply to the method for monitoring the processing of reusable medical devices that were already mentioned with respect to the user assistance system, and repetitions will therefore be omitted.

The location identifying feature can be saved in an RFID or NFC transponder, encoded in a barcode or a data matrix code, and/or consists of an external appearance of at least one stationary object.

The user identifying feature can be a password and/or biometric feature of the user.

Furthermore, instructions can be output as visual information that relate to the reprocessing of the medical device, and the execution of at least one of these instructions can be monitored by evaluating the image data recorded by the camera, wherein an error message can be output in the event that the instruction is incorrectly executed.

Light can be emitted by means of a light source within a wavelength range in which medical contaminants, such as blood or proteins, are excited to fluoresce, wherein by means of the camera, image data can be recorded within a wavelength range in which the fluorescence of the medical contaminants occurs, wherein furthermore fluorescent images can be generated, and these fluorescent images can be displayed on the projection surface.

According to one embodiment, navigation within the visual information that appears on the projection surface can be controlled by recognizing eye movements, gesture recognition, speech recognition and/or by mechanically actuating an input element on the housing of the data glasses.

The ongoing and completed reprocessing procedures can be recorded and documented, wherein the information relating to the ongoing and completed reprocessing procedures can be saved on an external data memory.

A designated processing time can be assigned to at least one reprocessing procedure, wherein the remaining duration of the designated processing time can be displayed on the projection surface, wherein upon the expiration of the designated processing time, information can be displayed on the projection surface relating to a position of a medical device whose designated processing time has expired.

Such object can further be achieved by a computer program with program code means which are adapted to execute a method having one or more of the aforementioned features.

BRIEF DESCRIPTION OF THE DRAWINGS

Further characteristics of the embodiments will become apparent from the description together with the claims and the included drawings. Embodiments can fulfill individual characteristics or a combination of several characteristics.

The embodiments are described below, without restricting the general idea of the invention, based on the exemplary embodiments in reference to the drawings, whereby we expressly refer to the drawings with regard to the disclosure of all details that are not explained in greater detail in the text. The following are shown in a schematic and simplified representation.

In the drawings, the same or similar types of elements and/or parts are provided with the same reference numbers so that a re-introduction will be omitted.

DETAILED DESCRIPTION

Figure 1:
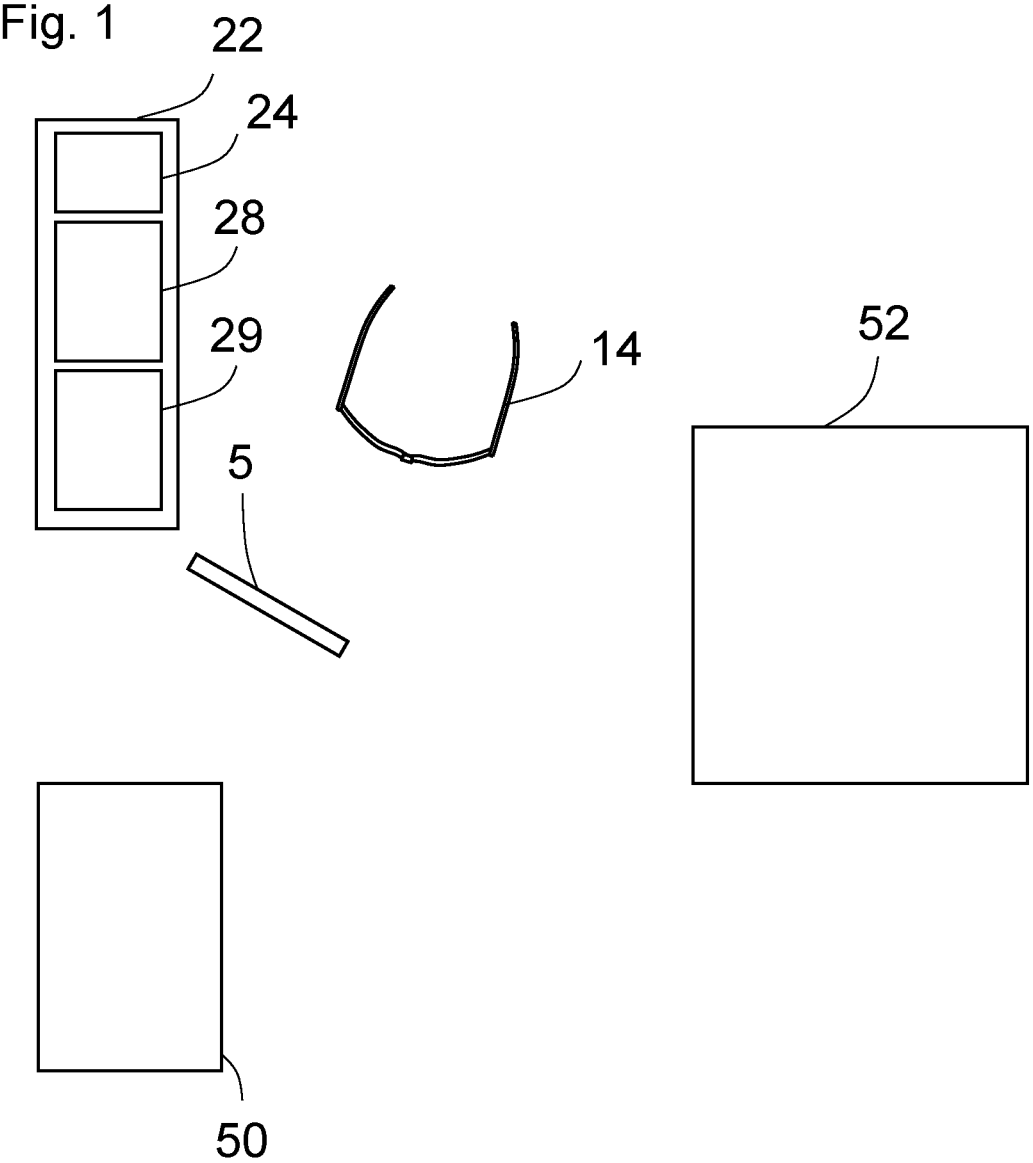
FIG. 1 illustrates a user assistance system.

FIG. 1 shows a schematic and simplified user assistance system comprising data glasses 14 and a data memory 28. The data memory 28 is shown in this example separate from the data glasses 14, for example as part of a server 22 that is connected by means of a wireless data connection to the data glasses 14. The server further comprises a processor 24. The user assistance system is used to process a reusable medical device 5, wherein the processing is carried out for example at several locations 50, 52. The locations 50, 52 are for example a processing machine and a sink.

Information relating to the ongoing and completed reprocessing procedures is saved on the external data memory 29 so that the processing is documented.

Figure 2:
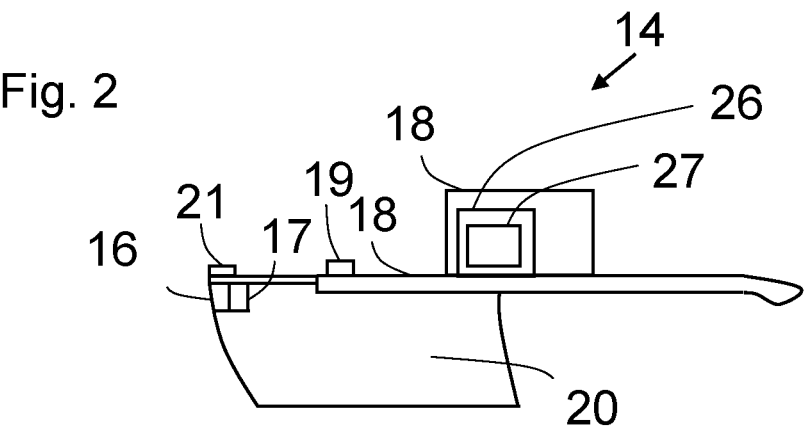
FIG. 2 illustrates data glasses.

In FIG. 2, the data glasses 14 are shown schematically and simplified in a side view. The data glasses 14 comprise a housing 18 and a projection surface 20 on which the data glasses 14 can reveal visual information in the form of text, images, videos or the like. The projection surface 20 is transparent within the range of visible light so that the user's field of vision is basically unrestricted.

The data glasses 14 moreover comprise a camera 16 aligned in the line of sight of the user, a camera 17 that basically records the eye region of the user, one or more microphones 19, and a light source 21. In addition, the data glasses 14 comprise a data processing device 26, which comprises a processor 27, arranged in the housing 18 on which a computer program is saved and can be executed to control the functions of the data glasses 14. By means of the camera 16, the data glasses 14 record image data and then evaluate these image data in the data processing device 26 in order to recognize identifying features 6, 41, 51, 53, objects, or persons determined in this manner. In addition, the position of objects in the space can also be determined. This makes it possible to reveal image signals on the projection surface 20 by means of which these objects can be emphasized from the perspective of the user.

The precise position of the cameras 16 and 17, the microphone or microphones 19 and the light source 21 on or in the housing 18 can be selected differently from the depiction in FIG. 2 as long as this does not restrict their function. The shape of the projection surface 20 can also deviate from the shape shown in FIG. 2. Moreover, a receiver with which an RFID or NFC signal can be received is located in the housing 18.

Figure 3:
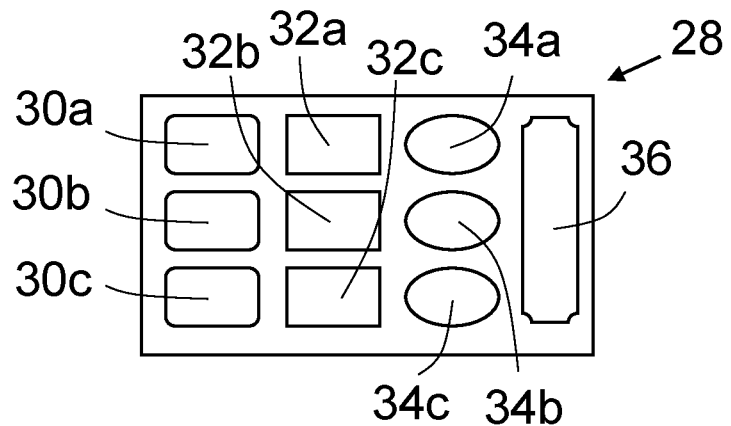
FIG. 3 illustrates a structure of a data memory.

The structure of a data memory 28 as can be used for the user assistance system is schematically portrayed in FIG. 3. Several type datasets 30a, 30b, 30c, several user datasets 32a, 32b, 32c, several location datasets 34a, 34b, 34c and information 36 regarding instructions for processing are saved on the data memory 28. Each type dataset 30a, 30b, 30c comprises information relating to a specific type of reusable medical device 5, each user dataset 32a, 32b, 32c comprises information relating to a specific user, and each location dataset 34a, 34b, 34c comprises information relating to a specific location.

Figure 4:
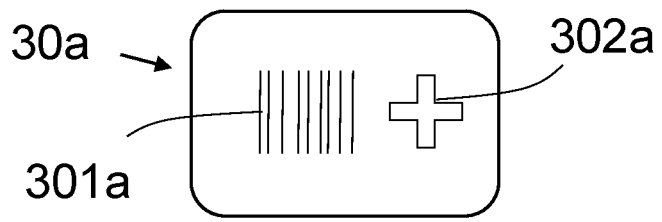
FIG. 4 illustrates a structure of a type dataset.
Figure 5:
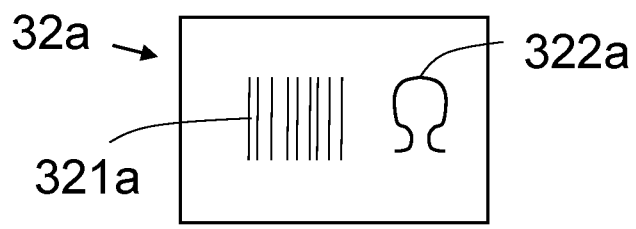
FIG. 5 illustrates a structure of a user dataset.
Figure 6:
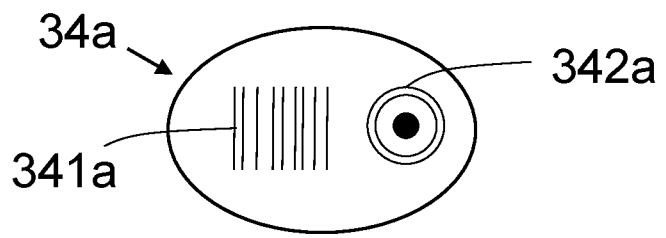
FIG. 6 illustrates a structure of the location dataset.

In FIGS. 4, 5 and 6, the type dataset 30a, the user dataset 32a and the location dataset 34a are portrayed schematically and as an example. Each dataset 30a, 32a, 34a comprises information 301a, 321a, 341a relating to at least one identifying feature 6, 41, 51, 53. In so doing, information 301a, 321a, 341a relating to several identifying features can also be saved in a dataset 30a, 32a, 34a. For example, information 301a on a first identifying feature 6 that is encoded in a barcode and a second identifying feature that is encoded in a data matrix code are saved in the dataset 30a, wherein both are assigned to the same type of medical device 5. In addition, the datasets 30a, 32a, 34a also comprise the type profile 302a, the user profile 322a and the location profile 342a. The structure of the data memory 28 shown in FIGS. 3, 4, 5 and 6 is only an example. Accordingly, for example the information 36 could also be saved in the type datasets 30a, 30b, 30c.

Figure 7:
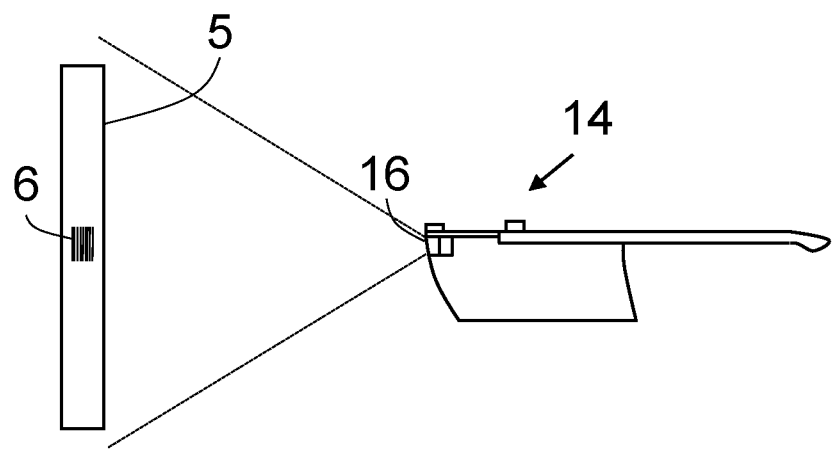
FIG. 7 illustrates an identification of a type of reusable medical devices.

FIG. 7 shows in a schematic and simplified manner how the recording of an identifying feature 6 of a reusable medical device 5 functions. In this example, the identifying feature 6 is encoded in a barcode that is recorded by means of the camera 16. Then this barcode is compared with the information 301a relating to the identifying features 6 saved in the type datasets 30a, 30b, 30c. If the recorded identifying feature 6 corresponds with the identifying feature 6 saved in the information 301a, the type profile 302a is activated which is assigned to the same type dataset 30a as the information 301a. Visual information then appears on the projection surface 20 of the data glasses 14 that relates to the processing of the associated type of reusable medical device 5.

Figure 8:
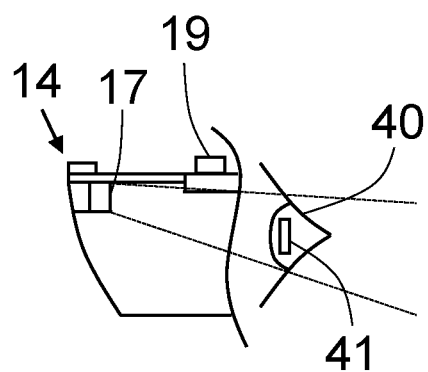
FIG. 8 illustrates an identification of a user.

The identification of a user by a user identifying feature 41 will be described in conjunction with FIG. 8. In the example shown in FIG. 7, the user identifying feature 41 is the iris pattern of the eye 40 of a user. By means of the camera 17, an image of the iris is recorded, and the image data are compared with the information 321a saved in the user datasets 32a, 32b, 32c. In the event of correspondence, an appropriate user profile 322a is activated, and the information displayed on the projection surface 20 is selected or restricted so that only the information relevant to the recognized user appears.

For example, speech and voice recognition can also be used for user identification. In so doing, the user is asked to speak a password. By means of the microphone 19, the spoken user password is recorded, and the password itself and/or the voice of the user can be compared with the information 321a. If such features correspond, i.e., the password and voice, the user profile 321a is activated.

Figure 9:
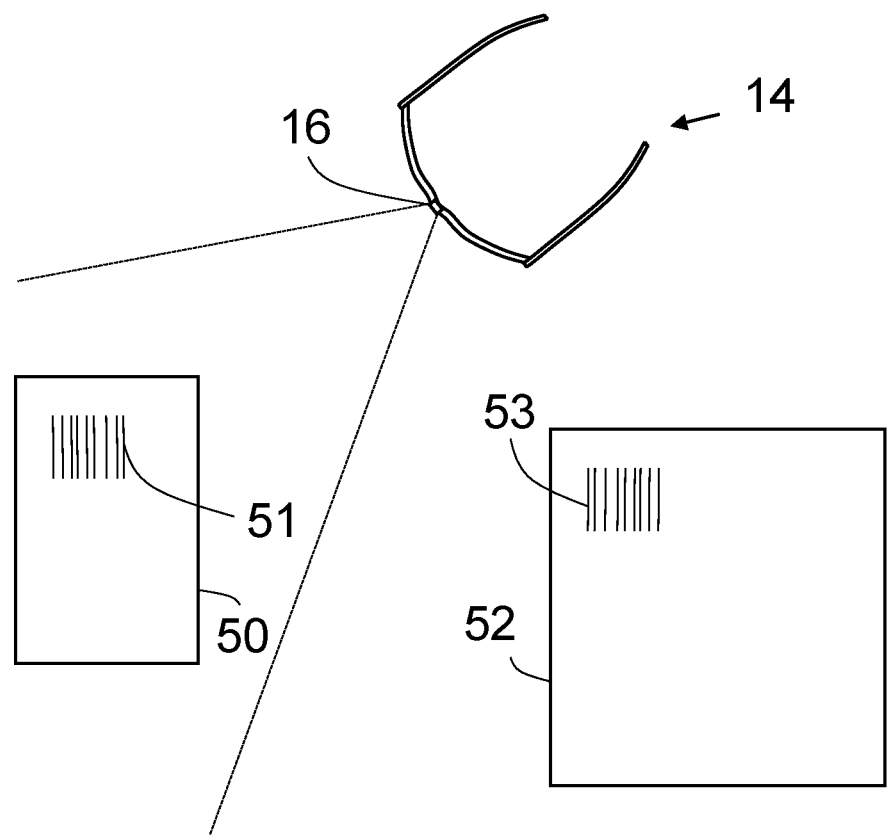
FIG. 9 illustrates an identification of a location.

FIG. 9 schematically portrays the identification of a location identifying feature 51, 53. Two locations 50, 52 are shown that can, for example, be a processing machine and a sink. Each location 50, 52 has a location identifying feature 51, 53. If a location identifying feature 51 is recorded by the data glasses 14, the location identifying feature 51 is compared with the information 341a saved in the location datasets 34a, 34b, 34c, and an associated location profile 342a is activated in the event of correspondence. Then only the information is revealed to the user that is relevant for processing the medical device 5 at the current location 50. If the user switches location so that he is then at location 52, the location identifying feature 53 is recorded, and the appropriate location profile which corresponds to this new location 52 is activated.

Accordingly, only the information appears for the particular user at his current location 50, 52 that is relevant for this user at this location 50, 52 for processing this type of medical device 5. An optimization of the processing procedure and a reduction of the errors while processing are thereby achieved.

Figure 10:
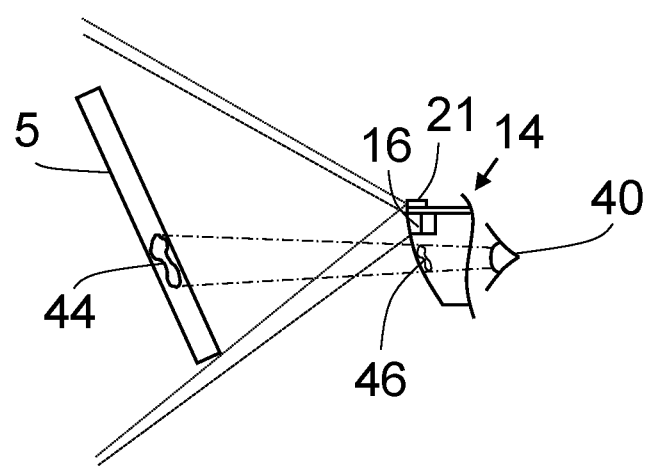
FIG. 10 illustrates a fluorescence function of the data glasses.

FIG. 10 shows how the result of processing can be monitored by the camera. Light is emitted by the light source 21 within a wavelength range in which contaminants 44, such as residual blood or protein, are excited to fluoresce. The illuminated range is shown in FIG. 10 by dotted lines. A fluorescence signal from the contaminants 44 is recorded by the camera 16 and then amplified in the data processing device of the data glasses 14. The data glasses 14 then show an amplified fluorescent image 46 on the projection surface 20. The user, illustrated by an eye 40, therefore perceives an amplified fluorescence of the residual blood or protein. In this manner, the user can easily recognize blood traces or residual proteins on a reusable medical device 5 to be cleaned and accordingly check the success of processing.

The user assistance system includes one or more processors 24, 27 each configured to carry out one or more functions of the method for monitoring the processing of reusable medical devices 5. In the embodiments discussed above, the processor 27 of the data glasses 14 projects visual information onto the projection surface arranged within the field of vision of a user of the data glasses useful in such processing.

The processor 27 of the data glasses 14 records an image of a reusable medical device 5 with the camera 17. The processor 24 of the server 22 then compares the image data of the image with the information relating to the identifying features in the type datasets 30a, 30b, 30c, identifies a type of the reusable medical device using the identifying feature available within the image, and activates a type profile assigned to an associated type dataset. The processor 27 of the data glasses 14 then records a user identifying feature and the processor 24 of the server 22 compares the user identifying feature with user datasets 32a, 32b, 32c saved on the data memory 28 which each comprise information relating to at least one user identifying feature and, in the event of correspondence, to activate a user profile assigned to the user dataset.

The processor 27 of the data glasses 14 also records record a location identifying feature and the processor 24 of the server 22 then compares the location identifying feature with location datasets 34a, 34b, 34c saved on the data memory 28 which each comprise information relating to at least one location identifying feature and, in the event of correspondence, activates a location profile assigned to the location dataset and retrieves information from the data memory 28 relating to instructions for reprocessing medical devices that are assigned to at least one type profile, at least one user profile and at least one location pros file.

The processor 27 of the data glasses 14 then displays the instructions for reprocessing the medical device assigned to the active type profile, the active user profile and the active location profile as visual information on the projection surface 20.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE SIGN LIST

5 Medical device
6 Identifying feature
14 Data glasses
16 Camera
17 Camera
18 Housing
19 Microphone
20 Projection surface
21 Light source
22 Server
24 Processor
26 Data Processing Device
27 Processor
28 Data memory
29 Data memory
30a, 30b, 30c Type dataset
32a, 32b, 32c User dataset
34a, 34b, 34c Location dataset
36 Information
40 Eye
41 User identifying feature
44 Contaminants
46 Fluorescent images
50 First location
51 First location identifying feature
52 Second location
53 Second location identifying feature
301a Information
302a Type profile
321a Information
322a User profile
341a Information
342a Location profile

What is claimed is:

1. A user assistance system for reprocessing reusable medical devices, the user assistance system comprising:
   data glasses comprising:
      a camera,
      an imaging optical module with a projection surface,
   a data memory in which a plurality of type datasets are saved that each comprise information relating to an identifying feature of a specific medical device type, and information relating to instructions for reprocessing the specific medical device type, and
   one or more processors configured to:
      project visual information onto the projection surface arranged within the field of vision of a user of the data glasses,
      record an image of a reusable medical device with the camera,
      compare the image data of the image with the information relating to the identifying features in the type datasets, identify a type of the reusable medical device using the identifying feature available within the image, activate a type profile assigned to an associated type dataset, record a user identifying feature and compare the user identifying feature with user datasets saved on the data memory which each comprise information relating to at least one user identifying feature and, in the event of correspondence, to activate a user profile assigned to the user dataset, record a location identifying feature and compare the location identifying feature with location datasets saved on the data memory which each comprise information relating to at least one location identifying feature and, in the event of correspondence, to activate a location profile assigned to the location dataset, retrieve information from the data memory relating to instructions for reprocessing medical devices that are assigned to at least one type profile, at least one user profile and at least one location profile, and display the instructions for reprocessing the medical device assigned to the active type profile, the active user profile and the active location profile as visual information on the projection surface.

2. The user assistance system according to claim 1, wherein the location identifying feature is one or more of saved in an RFID or NFC transponder, encoded in a barcode or a data matrix code, and consists of an external appearance of at least one stationary object.

3. The user assistance system according to claim 1, wherein the user identifying feature is one or more of a password and a biometric feature of the user.

4. The user assistance system according to claim 1, wherein the one or more processors are further configured to output instructions relating to the reprocessing of the medical device as visual information and to monitor execution of the instructions by evaluating the image data recorded by the camera.

5. The user assistance system according to claim 4, wherein the one or more processors are further configured to output an error message in the event that the instruction is incorrectly executed.

6. The user assistance system according to claim 1, further comprising a light source configured to emit excitation light within a wavelength range in which medical contaminants are excited to fluoresce, wherein the camera is configured to record images within the wavelength range in which the fluorescence of the medical contaminants occurs, wherein the one or more processors are further configured to generate fluorescent images and to display the fluorescent images on the projection surface.

7. The user assistance system according to claim 6, wherein the light source is configured to emit the excitation light within the wavelength range in which one or more of blood and proteins are excited to fluoresce.

8. The user assistance system according to claim 6, wherein the one or more processors are further configured to amplify the fluorescent images on the projection screen.

9. The user assistance system according to claim 1, further comprising an external memory configured to record and document an ongoing and a completed reprocessing procedure.

10. The user assistance system according to claim 1, wherein the one or more processors are further configured to assign a designated processing time to at least one reprocessing procedure and to display a remaining duration of a designated processing time on the projection surface.

11. The user assistance system according to claim 10, wherein upon expiration of the designated processing time, the one or more processors are further configured to display information on the projection surface relating to a position of a medical device whose designated processing time has expired.

12. A method for monitoring the processing of reusable medical devices, wherein a plurality of type datasets for different types of reusable medical devices and information relating to instructions on the reprocessing of the medical device types are saved in a data memory, and information is present in each type dataset relating to an identifying feature of a specific medical device type, the method comprising:

projecting visual information onto a projection surface arranged in a field of vision of a user of data glasses, recording at least one image of the reusable medical device with a camera, comparing image data of the image with the information relating to the identifying feature in the type datasets, identifying a type of the reusable medical device using an identifying feature available within the image, and activating a type profile assigned to an associated type dataset, recording a user identifying feature and comparing the user identifying feature with user datasets saved on the data memory which each comprise information relating to at least one user identifying feature and, in the event of correspondence, activating a user profile assigned to the user dataset, recording a location identifying feature and comparing the location identifying feature with location datasets saved on the data memory which each comprise information relating to at least one location identifying feature and, in the event of correspondence, activating a location profile assigned to the location dataset, and wherein the data memory comprises information relating to instructions for reprocessing the medical device that is assigned to at least one type profile, at least one user profile and at least one location profile, and the method further comprising displaying the instructions for reprocessing the medical device assigned to the active type profile, the active user profile and the active location profile as visual information on the projection surface.

13. The method according to claim 12, wherein instructions relating to the reprocessing of the medical device are output as visual information, and the execution of at least one of these instructions is monitored by evaluating the image data recorded by the camera.

14. The method according to claim 13, further comprising outputting an error message in the event that the instruction is incorrectly executed.

15. The method according to claim 12, further comprising emitting excitation light from a light source within a wavelength range in which medical contaminants are excited to fluoresce recording, with the camera, image data within the wavelength range in which the fluorescence of the medical contaminants occurs, generating fluorescent images, and displaying the fluorescent images on the projection surface.

16. The method according to claim 15, further comprising amplifying the displayed fluorescent images.

17. The method according to claim 12, further comprising recording and documenting ongoing and completed reprocessing procedures, and saving the information relating to the ongoing and completed reprocessing procedures in an external data memory.

18. The method according to claim 12, further comprising assigning a designated processing time to at least one reprocessing procedure, displaying a remaining duration of the designated processing time on the projection surface.

19. The method according to claim 18, further comprising displaying, upon the expiration of the designated processing time, information on the projection surface relating to a position of a medical device whose designated processing time has expired.

20. Non-transitory computer-readable storage medium storing instructions that cause a computer to at least perform the method of claim 12.

\* \* \* \* \*